(12) United States Patent
Kim et al.

(10) Patent No.: US 12,269,901 B2
(45) Date of Patent: Apr. 8, 2025

(54) PEPTIDE AND USE THEREOF

(71) Applicant: ENSOL BIOSCIENCES, INC., Daejeon (KR)

(72) Inventors: Hae Jin Kim, Daejeon (KR); Eun-Joung Moon, Daejeon (KR); Young Hoon Lee, Sejong (KR)

(73) Assignee: ENSOL BIOSCIENCES, INC., Daejeon (KR)

( * ) Notice: Subject to any disclaimer, the term of this patent is extended or adjusted under 35 U.S.C. 154(b) by 634 days.

(21) Appl. No.: 17/434,464

(22) PCT Filed: Mar. 5, 2020

(86) PCT No.: PCT/KR2020/003132
§ 371 (c)(1),
(2) Date: Aug. 27, 2021

(87) PCT Pub. No.: WO2020/184901
PCT Pub. Date: Sep. 17, 2020

(65) Prior Publication Data
US 2022/0135621 A1    May 5, 2022

(30) Foreign Application Priority Data

Mar. 13, 2019   (KR) .................. 10-2019-0028654

(51) Int. Cl.
*A61K 38/00*  (2006.01)
*A61P 1/18*   (2006.01)
*C07K 7/06*   (2006.01)

(52) U.S. Cl.
CPC .................................. *C07K 7/06* (2013.01); *A61P 1/18* (2018.01); *A61K 38/00* (2013.01)

(58) Field of Classification Search
CPC . A61K 38/00; A61P 1/18; A61P 29/00; C07K 7/06; C07K 7/08
See application file for complete search history.

(56) References Cited

U.S. PATENT DOCUMENTS

| | | |
|---|---|---|
| 2010/0256061 A1 | 10/2010 | Cruz et al. |
| 2011/0171178 A1 | 7/2011 | Levetan et al. |
| 2016/0002310 A1 | 1/2016 | Rosenberg |
| 2019/0389903 A1 | 12/2019 | Hahn et al. |

FOREIGN PATENT DOCUMENTS

| | | |
|---|---|---|
| CN | 102482323 A | 5/2012 |
| CN | 102892776 A | 1/2013 |
| CN | 104059131 A | 9/2014 |
| CN | 107787325 A | 3/2018 |
| EP | 1266964 A1 | 3/2001 |
| JP | 01250325 A | 10/1989 |
| JP | 2016519111 A | 6/2016 |
| KR | 10-2001-0108108 A | 12/2001 |
| KR | 10-2018-0092443 A | 8/2018 |
| KR | 20180092443 A * | 8/2018 |
| KR | 10-1903461 B1 | 10/2018 |
| RU | 2015143655 A | 4/2017 |
| WO | 2014/139472 A1 | 9/2014 |
| WO | 2018-147624 A1 | 8/2018 |

OTHER PUBLICATIONS

UniProt. sequence search. (Year: 2024).*
Zhu et al. The dual-function of bioactive peptides derived from oyster (*Crassostrea gigas*) proteins hydrolysates. Food Science and Human Wellness, 2023, 12(5): 1609-1617. (Year: 2023).*
Translation of KR20180092443A provided by Google patents (Year: 2018).*
Fangyi Zhao, et al., Conformation and self-assembly changes of isomeric peptide amphiphiles influenced by switching tyrosine in the sequences, Jun. 15, 2017, pp. 5189-5195, vol. 14-5, Journal of Materials Chemistry B.
Genbank, Accession No. XP_013302924.1, hypothetical protein NECAME_09019 [Necator americanus], Aug. 12, 2015, Genbank.
Pugliese, A., "Insulitis in the pathogenesis of type 1 diabetes", Pediatric Diabetes, 2016: 17 (Suppl. 22), pp. 31-36.
Rojas, Joselyn et al., "Pancreatic beta cell death: novel potential mechanisms in diabetes therapy", Journal of Diabetes Research, vol. 2018, Article ID 9601801, 19 pages.
Lennon, Greig P. et al., "T Cell Islet Accumulation in Type 1 Diabetes Is a Tightly Regulated, Cell-Autonomous Event", Immunity 31, Oct. 2009, pp. 643-653.
Ende, Norman et al., "Effect of human umbilical cord blood cells on glycemia and insulitis in type 1 diabetic mice", Biochemical and Biophysical Research Communications, 325 (2004), pp. 665-669.
Von Herrath, Matthias G. et al., "Interferong Is Essential for Destruction of b Cells and Development of Insulin-dependent Diabetes Mellitus", J. Exp. Med., vol. 185, No. 3, 1997, pp. 531-539.
Suk, Kyoungho et al., "IFN-gamma/TNF-alpha Synergism as the Final Effector in Autoimmune Diabetes: A Key Role for STAT1/IFN Regulatory Factor-1 Pathway in Pancreatic beta Cell Death", The Journal of Immunology, 2001; 166, pp. 4481-4489.
Piccirillo, Ciriaco A. et al., "TGF-beta1 Somatic Gene Therapy Prevents Autoimmune Disease in Nonobese Diabetic Mice", The Journal of Immunology, 1998; 161, pp. 3950-3956.
Lightfoot, Yaima L. et al., "Immune-mediated beta-cell death in type 1 diabetes: lessons from human beta-cell lines". European Journal of Clinical Investigation, 2012; 42(11): 1244-1251.

(Continued)

*Primary Examiner* — Aradhana Sasan
*Assistant Examiner* — Mercy H Sabila
(74) *Attorney, Agent, or Firm* — NKL LAW; Jae Youn Kim

(57) ABSTRACT

The present invention relates to a peptide consisting of the amino acid sequence of SEQ ID NO:1 or a pharmaceutically acceptable salt thereof and to the use thereof. The present invention is capable of effectively treating or preventing insulitis. Moreover, the present invention is capable of effectively treating or preventing type 1 diabetes.

5 Claims, 4 Drawing Sheets
Specification includes a Sequence Listing.

(56) References Cited

OTHER PUBLICATIONS

Fukushima et al: "Combined insulin B: 9-23 self-peptide and polyinosinic-polycytidylic acid accelerate insulitis but inhibit development of diabetes by increasing the proportion of $CD4^{+}Foxp3^{+}$ regulatory T cells in the islets in non-obese diabetic mice", Biochemical and Biophysical Research Communications, Elsevier, Amsterdam NL, vol. 367, No. 4, Jan. 14, 2008 (Jan. 14, 2008), pp. 719-724, XP022449863, ISSN: 0006-291X, DOI: 10.1016/J.BBRC. 2017.12.191 *abstract*.

* cited by examiner

[Fig. 1]
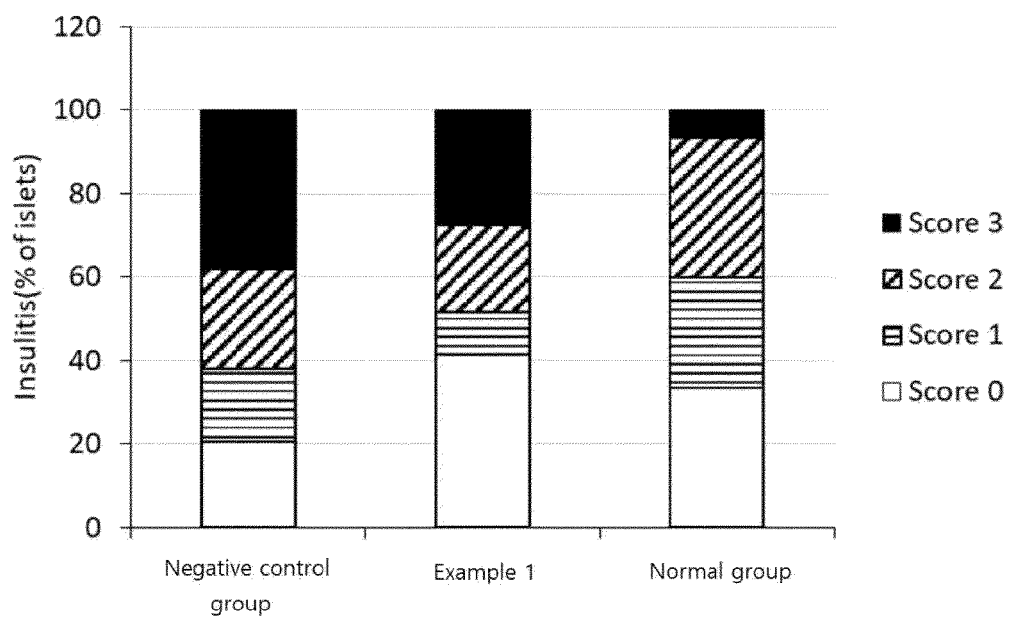
[Fig. 2]
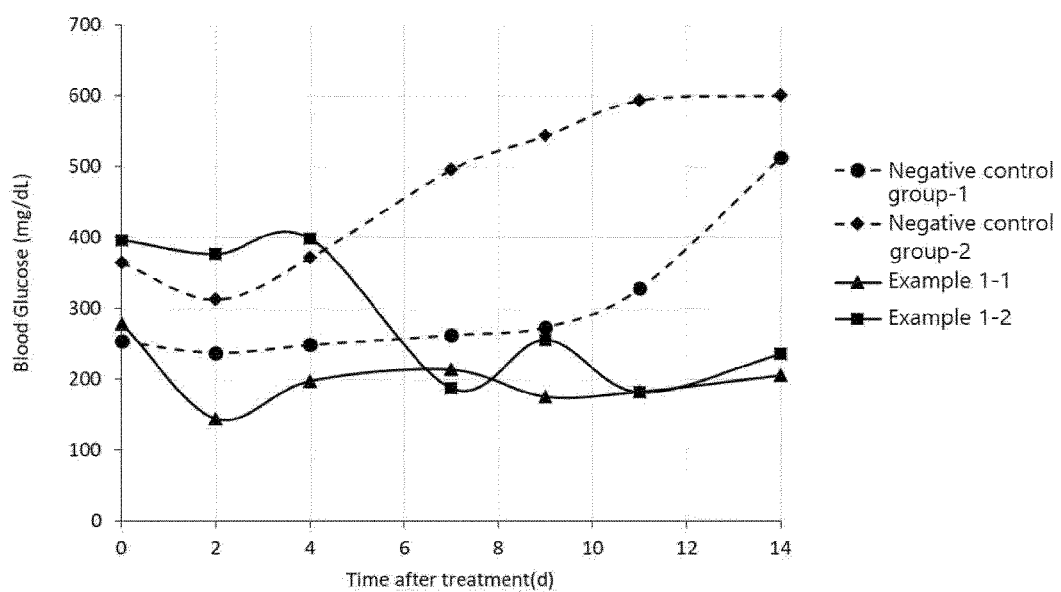

[Fig. 3]
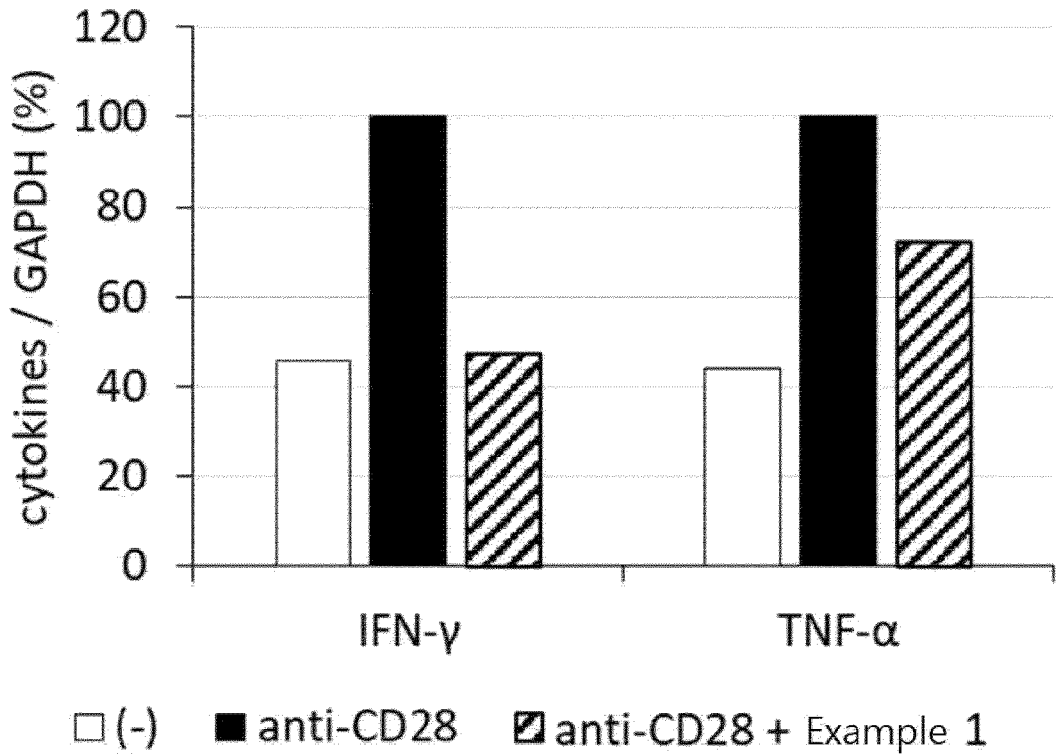
[Fig. 4]
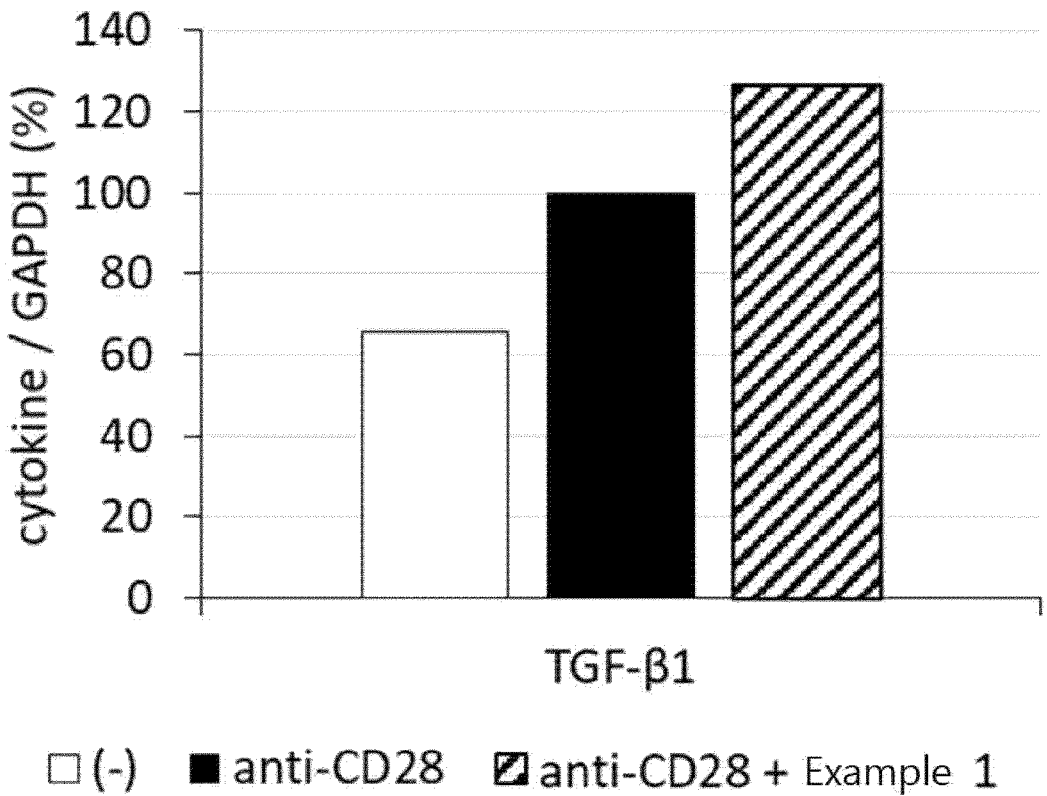

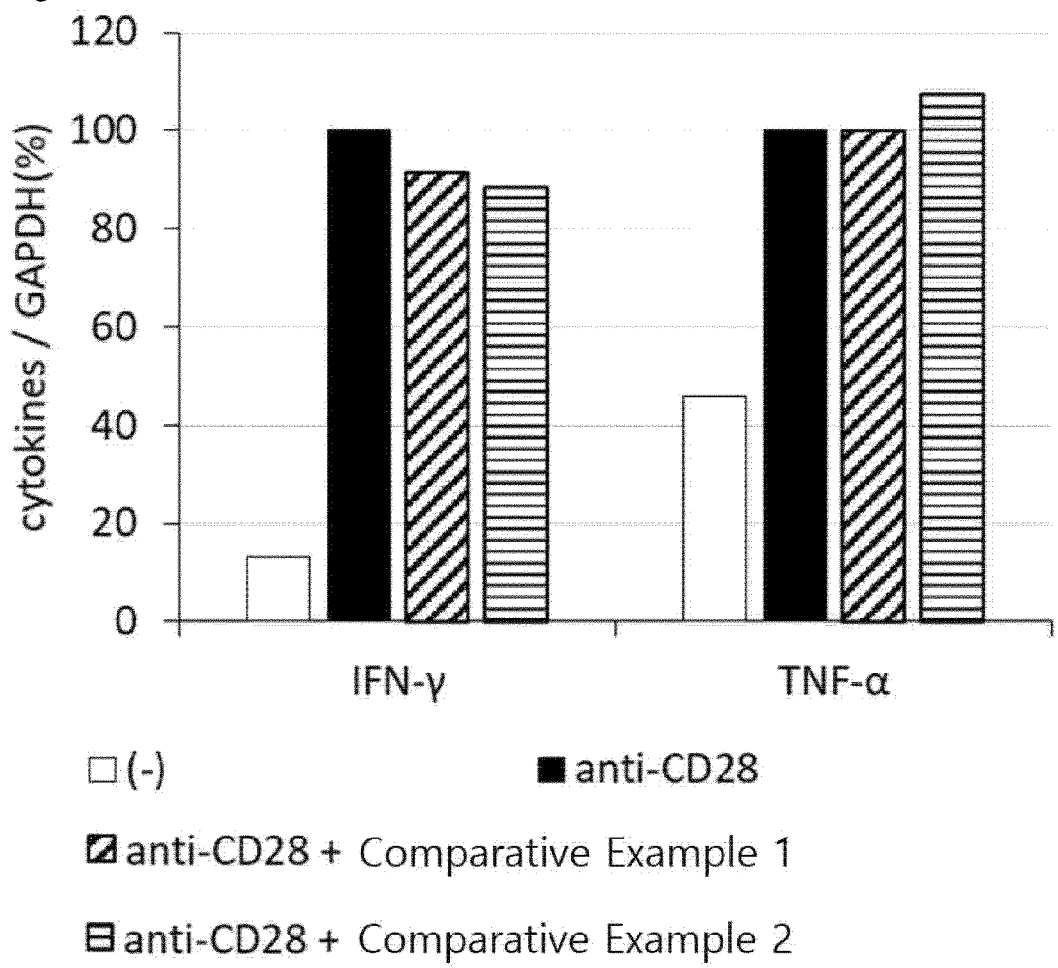
[Fig. 5]

[Fig. 6]
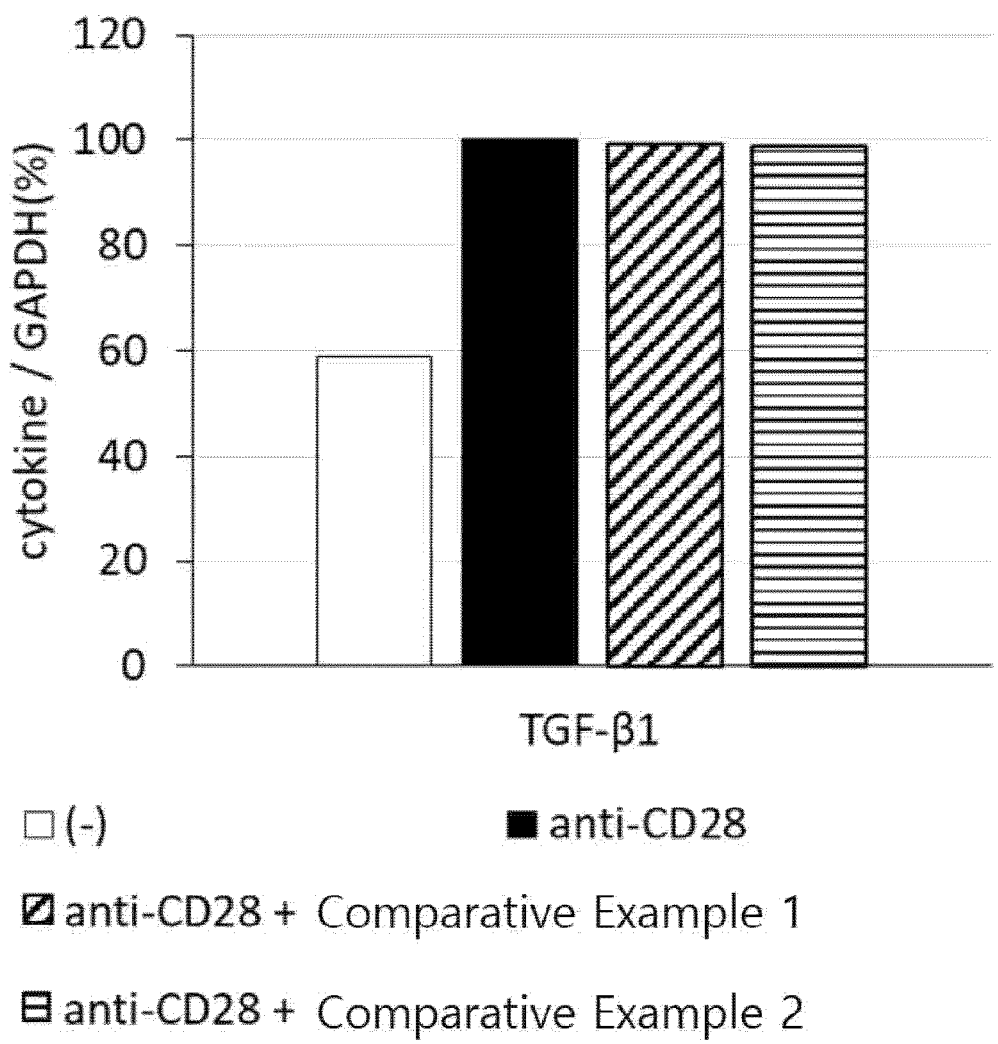

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: peptide

<400> SEQUENCE: 1

Tyr Gly Ala Gly Ala Gly Ala Gly Tyr
1               5

<210> SEQ ID NO 2
<211> LENGTH: 20
<212> TYPE: DNA
<213> ORGANISM: Artificial Sequence
<220> FEATURE:
<223> OTHER INFORMATION: forward primer for IFN-gamma

<400> SEQUENCE: 2
actggcaaaa ggatggtgac                                              20

<210> SEQ ID NO 3
<211> LENGTH: 20
<212> TYPE: DNA
<213> ORGANISM: Artificial Sequence
<220> FEATURE:
<223> OTHER INFORMATION: reverse primer for IFN-gamma

<400> SEQUENCE: 3
tgagctcatt gaatgcttgg                                              20

<210> SEQ ID NO 4
<211> LENGTH: 20
<212> TYPE: DNA
<213> ORGANISM: Artificial Sequence
<220> FEATURE:
<223> OTHER INFORMATION: forward primer for TNF-alpha

<400> SEQUENCE: 4
agcccccagt ctgtatcctt                                              20

<210> SEQ ID NO 5
<211> LENGTH: 20
<212> TYPE: DNA
<213> ORGANISM: Artificial Sequence
<220> FEATURE:
<223> OTHER INFORMATION: reverse primer for TNF-alpha

<400> SEQUENCE: 5
ctccctttgc agaactcagg                                              20

<210> SEQ ID NO 6
<211> LENGTH: 17
<212> TYPE: DNA
<213> ORGANISM: Artificial Sequence
<220> FEATURE:
```

```
<223> OTHER INFORMATION: forward primer for TGF-beta1

<400> SEQUENCE: 6
gcttcagctc cacagag                                                  17

<210> SEQ ID NO 7
<211> LENGTH: 17
<212> TYPE: DNA
<213> ORGANISM: Artificial Sequence
<220> FEATURE:
<223> OTHER INFORMATION: reverse primer for TGF-beta1

<400> SEQUENCE: 7
ggttgtagag ggcaagg                                                  17

<210> SEQ ID NO 8
<211> LENGTH: 20
<212> TYPE: DNA
<213> ORGANISM: Artificial Sequence
<220> FEATURE:
<223> OTHER INFORMATION: forward primer for GAPDH

<400> SEQUENCE: 8
tcatgaccac agtccatgcc                                               20

<210> SEQ ID NO 9
<211> LENGTH: 20
<212> TYPE: DNA
<213> ORGANISM: Artificial Sequence
<220> FEATURE:
<223> OTHER INFORMATION: reverse primer for GAPDH

<400> SEQUENCE: 9
tccaccaccc tgttgctgta                                               20

<210> SEQ ID NO 10
<211> LENGTH: 6
<212> TYPE: PRT
<213> ORGANISM: Artificial Sequence
<220> FEATURE:
<223> OTHER INFORMATION: peptide

<400> SEQUENCE: 10

Gly Ala Gly Ala Gly Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: peptide

<400> SEQUENCE: 11

Tyr Gly Ala Gly Ala Gly
1               5
```

PEPTIDE AND USE THEREOF

TECHNICAL FIELD

The present invention relates to a novel peptide, and more particularly to a novel peptide and the use thereof.

BACKGROUND ART

Lymphocytic infiltration of the pancreatic islet is called insulitis. Insulitis ultimately destroys pancreatic β-cells that secrete insulin, leading to type 1 diabetes (T1D) {Lennon G P, Bettini M, Burton A R, Vincent E, Arnold P Y, Santamaria P, Vignali D A. "T cell islet accumulation in type 1 diabetes is a tightly regulated, cell-autonomous event". Immunity. 2009 Oct. 16; 31(4):643-53, etc.}. Moreover, it has been reported that type 1 diabetes can be alleviated by protecting the pancreas from insulitis {Norman Ende, Ruifeng Chen, Alluru S. Reddi. "Effect of human umbilical cord blood cells on glycemia and insulitis in type 1 diabetic mice". Biochemical and Biophysical Research Communications 325 (2004) 665-669, etc.}.

Various cytokines such as IFN-γ (interferon-gamma), TNF-α (tumor necrosis factor-alpha) and TGF-β1 (transforming growth factor-beta1) are known to be involved in the development and suppression of insulitis. Insulitis is known to be caused by IFN-γ {von Herrath M G, Oldstone M B. "Interferon-γ is Essential for Destruction of β Cells and Development of Insulin-dependent Diabetes Mellitus". J. Exp Med. 1997 Feb. 3; 185(3):531-9, etc.}, and is also known to be caused by TNF-α {Kyoungho Suk, Sunshin Kim, Yun-Hee Kim, Kyoung-Ah Kim, Inik Chang, Hi deo Yagita, Minho Shong, Myung-Shik Lee. "IFN-γ/TNF-α Synergism as the Final Effector in Autoimmune Diabetes: A Key Role for STAT1/IFN Regulatory Factor-1 Pathway in Pancreatic β Cell Death". J. Immunol Apr. 1, 2001, 166 (7) 4481-4489, etc.}. Meanwhile, increased expression of TGF-β1 has been reported to protect non-obese diabetic (NOD) mice from insulitis {Piccirillo C A, Chang Y, Prud'homme G J. "TGF-β1 Somatic Gene Therapy Prevents Autoimmune Disease in Nonobese Diabetic Mice" J. Immunol. 1998 Oct. 15; 161(8):3950-6, etc.}.

Therefore, it is necessary to develop a material that has an effect on insulitis.

CITATION LIST

Non-Patent Literature (Non-Patent Document 1) Lennon G P, Bettini M, Burton A R, Vincent E, Arnold P Y, Santamaria P, Vignali D A. "T cell islet accumulation in type 1 diabetes is a tightly regulated, cell-autonomous event". Immunity. 2009 Oct. 16; 31(4):643-53.

(Non-Patent Document 2) Norman Ende, Ruifeng Chen, Alluru S. Reddi. "Effect of human umbilical cord blood cells on glycemia and insulitis in type 1 diabetic mice". Biochemical and Biophysical Research Communications 325 (2004) 665-669.

(Non-Patent Document 3) von Herrath M G, Oldstone M B. "Interferon-γ Is Essential for Destruction of β Cells and Development of Insulin-dependent Diabetes Mellitus". J. Exp. Med. 1997 Feb. 3; 185(3):531-9.

(Non-Patent Document 4) Kyoungho Suk, Sunshin Kim, Yun-Hee Kim, Kyoung-Ah Kim, Inik Chang, Hid eo Yagita, Minho Shong, Myung-Shik Lee. "IFN-γ/TNF-α Synergism as the Final Effector in Autoimmune Diabetes: A Key Role for STAT1/IFN Regulatory Factor-1 Pathway in Pancreatic β Cell Death". J. Immunol. Apr. 1, 2001, 166 (7) 4481-4489.

(Non-Patent Document 5) Piccirillo C A, Chang Y, Prud'homme G J. "TGF-β1 Somatic Gene Therapy Prevents Autoimmune Disease in Nonobese Diabetic Mice" J. Immunol. 1998 Oct. 15; 161(8):3950-6.

DISCLOSURE OF INVENTION

Technical Problem

An objective of the present invention is to provide a novel peptide.

Another objective of the present invention is to provide novel use of the peptide of the present invention.

The objectives of the present invention are not limited to the foregoing, and other objectives not mentioned herein will be clearly understood by those skilled in the art from the following description.

Solution to Problem

The present invention provides a peptide consisting of the amino acid sequence of SEQ ID NO:1 (YGAGAGAGY) or a pharmaceutically acceptable salt thereof.

In the amino acid sequence, Y represents tyrosine (Tyr), G represents glycine (Gly), and A represents alanine (Ala).

The amino acids that constitute the peptide include L-, D-, and DL-forms, all of which are incorporated in the amino acids of the peptide of the present invention. Also, it will be apparent that Y may be interpreted as having a meaning including 4-hydroxyphenylalanine, as well as tyrosine, as the amino acid.

The peptide includes variants thereof in which a portion of the peptide structure according to the present invention is varied by natural mutation or artificial mutation without changing the main activity thereof.

Examples of the pharmaceutically acceptable salt may include hydrochloride, sulfate, phosphate, acetate, citrate, tartrate, succinate, lactate, maleate, fumarate, oxalate, methane sulfonate, para-toluene sulfonate, sodium salt, potassium salt, calcium salt, and the like.

In addition, the present invention provides the use of the peptide or pharmaceutically acceptable salt thereof according to the present invention, and preferably the use thereof for the treatment or prevention of insulitis. Here, the term "treatment" comprehensively means the reduction or alleviation of symptoms, and the term "prevention" is used with a comprehensive meaning including inhibition of progression of a disease from an asymptomatic stage before expression of symptoms.

The treatment or prevention may be due to at least one selected from among inhibition of IFN-γ (interferon-gamma) expression, inhibition of TNF-α (tumor necrosis factor-alpha) expression, and induction of TGF-β1 (transforming growth factor-beta1) expression.

The inhibition of IFN-γ expression may be the inhibition of IFN-γ mRNA expression.

The inhibition of TNF-α expression may be the inhibition of TNF-α mRNA expression.

The induction of TGF-β1 expression may be the induction of TGF-β1 mRNA expression.

In addition, the present invention provides the use of the peptide or pharmaceutically acceptable salt thereof according to the present invention, and preferably the use thereof for the treatment or prevention of type 1 diabetes (T1D).

The type 1 diabetes may be caused by insulitis.

The treatment or prevention may be due to at least one selected from among inhibition of the development of insulitis and reduction thereof.

The treatment or prevention may be due to blood glucose reduction.

The blood glucose reduction may be due to at least one selected from among inhibition of the development of insulitis and reduction thereof.

In addition, the present invention provides a composition for the treatment or prevention of insulitis comprising the peptide or pharmaceutically acceptable salt thereof according to the present invention. Moreover, the present invention provides a composition for the treatment or prevention of type 1 diabetes comprising the peptide or pharmaceutically acceptable salt thereof according to the present invention. The composition may be a pharmaceutical composition.

The composition may comprise, as an active ingredient, the peptide or pharmaceutically acceptable salt thereof according to the present invention.

The composition further comprises a pharmaceutically acceptable additive, and may be composed of the peptide or pharmaceutically acceptable salt thereof according to the present invention and the pharmaceutically acceptable additive.

The peptide of the present invention may be prepared through methods typically used in the field of peptide chemistry. For example, the peptide may be prepared with reference to literature widely known in the art, or through a method such as solution-phase synthesis or solid-phase synthesis.

Examples of the process for forming a peptide bond may include an acyl azide method, an acyl halide method, an acyl imidazole method, a carbodiimide method, a phosphonium method, an anhydride method, a mixed anhydride method, an oxidation-reduction method, and the use of Woodward's reagent K.

Before the condensation reaction, a carboxyl group, an amino group or the like, not participating in the reaction, may be protected, and a carboxyl group that participates in the condensation reaction may be activated through methods known in the art.

Examples of the functional group for protecting the carboxyl group may include ester-forming groups, such as methyl, tert-butyl, aryl, pentafluorophenyl, benzyl, para-methoxybenzyl, and methoxyethoxymethyl.

Examples of the functional group for protecting the amino group may include trityl carbonyl, aryloxycarbonyl, cyclohexyloxycarbonyl, trichloroethyloxycarbonyl, benzyloxycarbonyl, tert-butoxycarbonyl, and/or 9-fluorenylmethyloxycarbonyl.

Examples of the active form of the carboxyl group may include mixed anhydride, azide, acyl chloride, and active ester [ester with alcohol (e.g. pentachlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide, or 1-hydroxybenzotriazole)].

Solvents usable in the condensation reaction for forming a peptide bond may include benzene, toluene, hexane, acetone, nitromethane, cyclohexane, ether, chloroform, dichloromethane, ethyl acetate, N,N-dimethylformamide, dimethylsulfoxide, pyridine, dioxane, tetrahydrofuran, water, methanol, and ethanol, which may be used alone or in combination.

The reaction temperature may fall in the range of about −70° C. to 100° C., which is typically applied in the reaction, and preferably falls in the range of −30° C. to 30° C.

The deprotection reaction for removing the protective group from the peptide may be carried out using an acid compound, a base compound, or a transition metal, capable of removing the protective group without influencing the peptide bond, depending on the kind of protective group.

The deprotection reaction may be performed through acid treatment using, for example, hydrogen chloride, hydrogen bromide, hydrogen fluoride, acetic acid, methanesulfonic acid, trifluoromethanesulfonic acid, trifluoroacetic acid, trimethylchlorosilane, or mixtures thereof.

When the deprotection reaction is carried out through acid treatment, it may be promoted by the addition of an adjuvant such as anisole, phenol or thioanisole.

Alternatively, the deprotection reaction may be performed through base treatment using, for example, ammonia, diethylamine, hydrazine, morpholine, N-methylpyrrolidine, piperidine, sodium carbonate, or mixtures thereof.

Alternatively, the deprotection reaction may be performed through transition metal treatment using, for example, zinc, mercury, palladium/hydrogen, etc.

After completion of the reaction, the peptide may be purified using a typical peptide purification process, such as extraction, layer separation, solid precipitation, recrystallization, or column chromatography.

Moreover, the peptide according to the present invention may be converted into a variant thereof or a pharmaceutically acceptable salt thereof using a typical process.

The peptide according to the present invention may be synthesized using an automatic peptide synthesizer, or may be produced through genetic manipulation. For example, a fusion gene encoding a fusion protein comprising a fusion partner and the peptide according to the present invention is manufactured through genetic manipulation, and is then used to transform a host microorganism, and the fusion protein is expressed in the host microorganism, after which the peptide according to the present invention is cleaved or separated from the fusion protein using a proteolytic enzyme or compound, thus yielding a desired peptide.

The peptide or pharmaceutically acceptable salt thereof according to the present invention is parenterally administered in an amount of 24.3 mg/day to 4860 mg/day, and preferably 48.6 mg/day to 2430 mg/day. Upon oral administration, the amount thereof corresponds to 5 to 10 times the amount upon parenteral administration. The administration may be conducted once a day or several times a day, and the amount thereof may be based on an adult (weighing 60 kg), but may vary depending on the weight, body condition, and the like. The peptide or pharmaceutically acceptable salt thereof according to the present invention may be mainly administered through parenteral routes, for example, intravenous injection, subcutaneous injection, intraspinal administration, transdermal administration, transnasal administration or intrarectal administration. In some cases, oral administration is possible.

The peptide or pharmaceutically acceptable salt thereof, or the composition according to the present invention may be formulated, together with a pharmaceutically acceptable additive, into an injection, a suppository, a powder, a nose drop, a granule, a tablet, or a transdermal patch.

The pharmaceutically acceptable additive may be applied depending on a variety of factors well known to those skilled in the art, including, for example, a specific bioactive material, its concentration, stability and intended bioavailability; disorders and diseases to be treated or conditions associated therewith; individuals to be treated, their age, size, and general health status; and composition administration routes, for example, nasal, oral, ocular, topical, transdermal and muscular routes, but the present invention is not limited thereto. The pharmaceutically acceptable additive, which is used for administration of the bioactive material, in addition to the oral administration route, may include an aqueous solution including D5W (5% glucose in water), dextrose and a physiological salt in an amount within 5% of the volume thereof. For topical intralesional injection, any injectable hydrogel may be used to enhance the therapeutic effects and increase the duration thereof. Also, the pharmaceutically acceptable additive may comprise additional components for improving the stability of effective components such as preservatives and antioxidants. The peptide or pharmaceutically acceptable salt thereof or the composition according to the present invention may be formulated through appropriate methods in the related field, and is preferably formulated so as to be suitable for each disease or component with reference to widely known literature regarding formulation methods in the art.

The peptide of the present invention may be stored in a saline solution, or may be lyophilized in an ampoule after the addition of mannitol or sorbitol, and may be administered after dissolution in saline.

In addition, the present invention provides a method of treating or preventing insulitis, including administering the peptide or pharmaceutically acceptable salt thereof according to the present invention to a mammal, including a human, in need of administration. In addition, the present invention provides a method of treating or preventing type 1 diabetes, including administering the peptide or pharmaceutically acceptable salt thereof according to the present invention to a mammal, including a human, in need of administration. In addition, the present invention provides the use of the peptide or pharmaceutically acceptable salt thereof according to the present invention for the manufacture of a medicament for the treatment or prevention of insulitis. In addition, the present invention provides the use of the peptide or pharmaceutically acceptable salt thereof according to the present invention for the manufacture of a medicament for the treatment or prevention of type 1 diabetes. The administered peptide or pharmaceutically acceptable salt thereof may be a peptide or pharmaceutically acceptable salt thereof in an effective amount.

Unless otherwise mentioned, the matters described in connection with the peptide or pharmaceutically acceptable salt thereof, as well as the use, the composition, and the method according to the present invention, are applied equally to each other in the same scope unless they are contradictory to each other.

Advantageous Effects of Invention

According to the present invention, insulitis can be effectively treated or prevented. Moreover, according to the present invention, type 1 diabetes can be effectively treated or prevented.

BRIEF DESCRIPTION OF DRAWINGS

FIG. 1 is a graph showing the results of analysis of the effect of the peptide of Example 1 on inhibiting or reducing the development of insulitis;

FIG. 2 is a graph showing the results of analysis of the effect of the peptide of Example 1 on lowering blood glucose levels;

FIG. 3 is a graph showing the results of analysis of the effect of the peptide of Example 1 on inhibiting IFN-γ expression and TNF-α expression;

FIG. 4 is a graph showing the results of analysis of the effect of the peptide of Example 1 on inducing TGF-β1 expression;

FIG. 5 is a graph showing the results of analysis of the effects of the peptides of Comparative Example 1 and Comparative Example 2 on inhibiting IFN-γ expression and TNF-α expression; and FIG. 6 is a graph showing the results of analysis of the effects of the peptides of Comparative Example 1 and Comparative Example 2 on inducing TGF-β1 expression.

MODE FOR THE INVENTION

A better understanding of the present invention is given through the following examples, comparative examples and preparation examples, in which the examples and preparation examples are merely set forth to illustrate the present invention but are not to be construed as limiting the scope of the present invention.

The reagents used in the following examples and the like are commercially available and top-quality products, and are purchased from Sigma-Aldrich, unless otherwise mentioned.

<Example 1> Preparation of Peptide

The peptide shown in Table 1 below was prepared using a solid-phase peptide synthesis method. Specifically, the peptide was synthesized using a solid-phase method using the chemical properties of Fmoc (9-fluorenyl-methoxycarbonyl).

More specifically, 0.55 mmol/g of a solid resin (Wang resin; Sigma-Aldrich), 5 ml of dimethylformamide (DMF), 1.1 mmol of Fmoc-Tyr(tBu)-OH and 0.55 mmol of O-benzotriazole-N,N,N',N'-tetramethyl-uronium-hexafluoro-phosphate (HBTU) were placed in a well-dried reactor and stirred at room temperature for 2 hr, thus synthesizing a Fmoc-Tyr(tBu)-resin, after which the synthesized resin was filtered and then washed with dimethylformamide. The washed resin was added with 8 ml of a 20% piperidine solution (dissolved in dimethylformamide) and stirred at room temperature for 30 min, thus synthesizing a Fmoc (fluorenylmethyloxycarbonyl-protecting group)-deprotected Tyr(tBu)-resin. The synthesized Tyr(tBu)-resin was filtered and then washed with dimethylformamide.

The washed Tyr(tBu)-resin was added with 5 ml of dimethylformamide, 1.1 mmol of Fmoc-Gly-OH and 0.55 mmol of O-benzo-triazole-N,N,N',N'-tetramethyl-uronium-hexafluoro-phosphate (HBTU) and stirred at room temperature for 2 hr, thus synthesizing a Fmoc-Gly-Tyr(tBu)-resin, after which the synthesized resin was filtered and then washed with dimethylformamide. The washed resin was added with 8 ml of a 20% piperidine solution (dissolved in dimethylformamide) and stirred at room temperature for 30 min, thus synthesizing a Fmoc-deprotected Gly-Tyr(tBu)-resin. The synthesized Gly-Tyr(tBu)-resin was filtered and then washed with dimethylformamide. Through these procedures, a peptide bond was formed between glycine and tyrosine.

Thereafter, Fmoc-Ala-OH, Fmoc-Gly-OH, Fmoc-Ala-OH, Fmoc-Gly-OH, Fmoc-Ala-OH, Fmoc-Gly-OH, and Fmoc-Tyr(tBu)-OH were sequentially used, and the same procedures as those for forming the peptide bond between glycine and tyrosine were repeated, thereby preparing a peptide-resin compound comprising the amino acid sequence shown in Table 1 below.

Thereafter, the compound was added with 10 ml of a mixed solution of trifluoroacetic acid and water at a ratio of 95:5 (v/v), stirred at room temperature for 3 hr, and then filtered, after which the resulting filtrate was added with diethylether to thus crystallize a solid. The solid thus obtained was filtered, washed with diethylether and then dried, thus synthesizing a crude peptide compound comprising the amino acid sequence shown in Table 1 below.

The crude peptide compound was purified through reverse-phase high-performance liquid chromatography (RP-HPLC) using a Shimadzu 5 mm Shim-pack ODS C18 column (20×250 mm) and lyophilized, thus yielding the peptide of Example 1 in a white solid form.

The purified peptide was identified via analytical RP-HPLC using a Shim-pack 5 mm ODS C18 column (4.6×250 mm), and the molecular weight of the peptide was measured using a matrix-assisted laser desorption ionization (MALDI)-mass spectrometer (Axima CFR, Kratos Analytical, Manchester, UK).

TABLE 1

| | Amino acid sequence | SEQ ID NO: |
|---|---|---|
| Example 1 | YGAGAGAGY | 1 |

In Table 1, Y represents tyrosine (Tyr), G represents glycine (Gly), and A represents alanine (Ala).

<Example 2> Evaluation of Peptide Effects 2-1. Evaluation of Effect of Inhibiting or Reducing Development of Insulitis The effect of the peptide of Example 1 on inhibiting or reducing the development of insulitis was experimentally verified.

The experimental animals were 8-week-old female NOD/ShiLtJ (Jackson Lab). NOD (Non-obese diabetic) mice are animal models of insulitis and type 1 diabetes. In these animals, it is known that type 1 diabetes occurs at 18 weeks of age on average and 90% of incidence thereof occurs by 30 weeks of age. All animals were housed under SPF barrier conditions. This study was approved by the Institutional Animal Care and Use Committee of Osong Medical Innovation Foundation Laboratory Animal Center (Kbio-IA-CUC-2018-066). The acclimation period was 1 week, and the light/dark cycle was 12 hr (08:00 lights off-20:00 lights on). The temperature was 20±2° C., and the relative humidity was 60 to 80%. Since the incidence of diabetes may be inhibited by intestinal microorganisms, water, the pH of which was adjusted to 2.8-3.2 using HCl, was supplied to the experimental animals.

The end of the tail of the experimental animals prepared above was wounded once a week and a drop of blood therefrom was measured for blood glucose levels using a glucometer (Roche, Accu-CHEK Performa). When the blood glucose levels were measured to be 250 mg/dL or more and the blood glucose levels remeasured on the third day thereafter was also 250 mg/dL or more, type 1 diabetes was considered to have occurred, and the experiment was conducted.

Two experimental animals with type 1 diabetes were selected as the treatment group of Example 1, and were subcutaneously (SC) administered with 100 μl of the peptide of Example 1 (5 mg/kg). The administration was performed every morning and evening for 14 days, and the blood glucose levels were measured using a glucometer. The administration was stopped when the blood glucose level decreased to 250 mg/dL or less. In addition, two experimental animals with type 1 diabetes were selected as a negative control group, and were treated in the same manner as the treatment group of Example 1, with the exception that PBS (phosphate-buffered saline, Welgene) was administered in lieu of the peptide of Example 1. On the $14^{th}$ day, one experimental animal, the blood glucose levels of which were measured to be less than 250 mg/dL, was selected as a normal group, and was used to compare the insulitis scores of experimental animals with type 1 diabetes and experimental animals without type 1 diabetes.

After measurement of the blood glucose levels on the $14^{th}$ day, the pancreas was removed from the experimental animals and fixed in 10% natural buffered formalin (10% NBF, Sigma, HT5011) to manufacture a paraffin block. The fixed pancreatic tissue was sliced, stained with hematoxylin and eosin (H&E), and observed using an optical microscope to confirm the development of insulitis. Insulitis was divided into 4 stages depending on the extent thereof, stage 0 in which insulitis is not observed, stage 1 in which insulitis is observed around the pancreatic islets, stage 2 in which insulitis of less than 75% is observed, and stage 3 in which insulitis of 75% or more is observed. For the treatment group of Example 1, the number of islets in two animals was measured, individual islets were classified depending on the stage of insulitis to thus determine the insulitis score, and the number of islets corresponding to each insulitis stage among the total number of islets was represented as a percentage. For the negative control group and the normal group, the insulitis scores were determined as in the treatment group of Example 1, after which the number of islets corresponding to each insulitis stage among the total number of islets was represented as a percentage. The results thereof are shown in FIG. 1.

FIG. 1 is a graph showing the results of analysis of the effect of the peptide of Example 1 on inhibiting or reducing the development of insulitis. In FIG. 1, the x axis represents each group, and the y axis represents the insulitis score {insulitis (% of islets)}. In FIG. 1, Score 0 means stage 0, Score 1 means stage 1, Score 2 means stage 2, and Score 3 means stage 3.

As shown in FIG. 1, in the treatment group of Example 1, the percentage in stage 3, which is the most severe stage, was decreased, and the percentages in stages 0-2, which may secrete insulin, were increased compared to the negative control group. In particular, in the treatment group of Example 1, the percentage in stage 0, in which insulitis did not occur, was approximately doubled compared to the negative control group. Based on the above results, it can be found that the peptide of Example 1 was effective at treating insulitis by inhibiting the development of insulitis and alleviating insulitis. Moreover, the percentage of stage 0 was higher in the treatment group of Example 1 than in the normal group. Therefore, the peptide of Example 1 was capable of inhibiting the development of insulitis, indicating that the peptide of Example 1 was effective at both treating and preventing insulitis.

Ultimately, it can be concluded that the peptide of the present invention has a therapeutic and/or prophylactic effect on insulitis.

2-2. Evaluation of Effect of Lowering Blood Glucose Levels

In order to evaluate the effect of the peptide of Example 1 on type 1 diabetes (T1D), the effect of the peptide of Example 1 on lowering blood glucose levels in experimental animals with type 1 diabetes was experimentally verified.

Specifically, the blood glucose levels of the treatment group of Example 1 and the negative control group, among the experimental animals of Example 2-1, were analyzed, and thus the effect of the peptide of Example 1 on lowering the blood glucose levels was evaluated. The results thereof are shown in FIG. 2.

FIG. 2 is a graph showing the results of analysis of the effect of the peptide of Example 1 on lowering blood glucose levels. Here, the x axis represents the time after treatment (d), and the y axis represents blood glucose levels (mg/dL).

As shown in FIG. 2, the blood glucose levels of the two animals in the treatment group of Example 1 (Example 1-1 and Example 1-2) decreased significantly and then remained in the normal range, but the blood glucose levels of the two animals in the negative control group (Negative control group-1 and Negative control group-2) continuously increased.

Based on the above results, it can be confirmed that the peptide of the present invention was effective at lowering blood glucose levels. Since the peptide of the present invention is effective at lowering the blood glucose levels of mice with type 1 diabetes and maintaining the normal blood glucose levels, the peptide of the present invention appears to be able to treat or prevent type 1 diabetes by lowering the blood glucose levels. Moreover, as confirmed above, since the peptide of the present invention is capable of inhibiting and reducing the development of insulitis, it can exhibit a therapeutic and/or prophylactic effect on type 1 diabetes by the action thereof, and can be considered to have an effect of lowering blood glucose levels.

Ultimately, it can be concluded that the peptide of the present invention enables the treatment and/or prevention of type 1 diabetes.

2-3. Evaluation of Effect of Inhibiting IFN-γ Expression and TNF-α Expression and Inducing TGF-β1 Expression The effect of the peptide of Example 1 on cytokine {IFN-γ (interferon-gamma), TNF-α (tumor necrosis factor-alpha) and TGF-β1 (transforming growth factor-beta1)} associated with insulitis was evaluated. Insulitis is known to be caused by the expression of IFN-γ and TNF-α, and increased expression of TGF-β1 is known to protect the pancreas from insulitis. Thus, by measuring whether the peptide of Example 1 inhibits IFN-γ and TNF-α expression and induces TGF-β1 expression, the effect thereof on insulitis was evaluated.

The end of the tail of the experimental animals prepared as in Example 2-1 was wounded once a week, and a drop of blood therefrom was measured for blood glucose levels using a glucometer (Roche, Accu-CHEK Performa). The blood glucose levels were confirmed to be "high" (600 mg/dL or more), the mice were subjected to cervical dislocation, and the spleen was extracted therefrom. A cell strainer (BD, 352350) was placed on a 50 ml tube, and the extracted spleen tissue was passed through the cell strainer using the plunger end of a syringe, after which the tube containing the strained cells was added with HBSS (Hanks' Balanced Salt solution) so that the cells were washed with water, followed by centrifugation (1,000 rpm, 5 min) to remove the supernatant. The cells were suspended with 1 ml of HBSS, added with 10 ml of 1×RBC lysis buffer (Ebioscience, 00-4333-57), mixed with gentle stirring, allowed to stand in ice for 5 min, and then centrifuged (1,000 rpm, 5 min) to remove the supernatant. The resulting cells were added with 10 ml of a RBC lysis buffer once more, allowed to stand in ice for 5 min, further centrifuged (1,000 rpm, 5 min) to remove the supernatant, and then washed two times with 10 ml of HBSS. After final centrifugation (1,000 rpm, 5 min), the cells were suspended with 1 ml of HBSS, 50 μl of the cells were diluted with a trypan blue solution at 1:1, and the number of cells was counted using a hemocytometer. The separated splenocytes were placed in an amount of $1×10^7$ cells per well in a 6-well plate in 2 ml of an RPMI-1640 (Welgene, LM011-01) medium containing 10% FBS (fetal bovine serum, Corning, 35-015-CV), and 2 ng/ml of anti-mouse CD28 (Ebioscience, 16-0281-82) for inducing activity of T cells was added thereto. Simultaneously, the cells were treated with 100 mM of the peptide of Example 1 in a 5% $CO_2$ incubator at 37° C. for 3 hr to evaluate changes in the expression of IFN-γ and TNF-α and for 72 hr to evaluate changes in the expression of TGF-β1.

Thereafter, the cells were centrifuged (1,000 rpm, 5 min) to remove the supernatant, lysed through pipetting with 5 ml of TRIzol (Invitrogen, 15596-018), and allowed to stand at room temperature for 5 min. The cells were added with 100 μl of chloroform, mixed with vigorous stirring, and then allowed to stand at room temperature for 2 min. Thereafter, centrifugation (12,000 rpm, 15 min) was performed, and only the supernatant was cautiously transferred to a new 1.5 ml e-tube, added with 300 μl of iso-propanol, mixed with gentle stirring, and then allowed to stand at room temperature for 10 min. Then, centrifugation (12,000 rpm, 15 min) to remove the supernatant, washing with 500 μl of 70% ethanol diluted in DEPC (diethyl pyrocarbonate)-treated water (LPS solution, CBW004), and centrifugation (12,000 rpm, 10 min) to remove the supernatant were conducted, after which the remaining ethanol was evaporated in the uncovered state. RNA was eluted by adding 30 μl of DEPC-treated water and quantified.

cDNA was synthesized through the experimental procedure for a cDNA synthesis kit (ELPISbio, EBT-1512) using 1 mg of the quantified RNA. Then, in accordance with the procedure for a PCR (Polymerase Chain Reaction) kit (Solgent, SEF01-M50H), cDNA of each cytokine (IFN-γ, TNF-α, TGF-β1) and a housekeeping gene GAPDH for quantitative determination of changes in cytokine expression were amplified. Then, the PCR products were electrophoresed on a 2% agarose gel to thus confirm DNA bands, which were then quantified using an Image J program, and the quantified values were calculated as the percentage relative to GAPDH. The control group was treated in the same manner as the treatment group of Example 1, with the exception that PBS (phosphate-buffered saline, Welgene) was used in lieu of the peptide of Example 1 and anti-mouse CD28, and the negative control group was treated in the same manner as the treatment group of Example 1, with the exception that PBS (phosphate-buffered saline, Welgene) was used in lieu of the peptide of Example 1. The results thereof are shown in FIGS. 3 and 4. The primer sequences for PCR of each cytokine are shown in Table 2 below.

TABLE 2

| Cytokine | | Base sequence | SEQ ID NO: |
|---|---|---|---|
| IFN-γ | forward | actggcaaaaggatggtgac | 2 |
| | reverse | tgagctcattgaatgcttgg | 3 |
| TNF-α | forward | agcccccagtctgtatcctt | 4 |
| | reverse | ctcccttttgcagaactcagg | 5 |
| TGF-β1 | forward | gcttcagctccacagag | 6 |
| | reverse | ggttgtagagggcaagg | 7 |
| GAPDH | forward | tcatgaccacagtccatgcc | 8 |
| | reverse | tccaccacctgttgctgta | 9 |

In Table 2, t represents thymine, a represents adenine, c represents cytosine, and g represents guanine.

FIG. 3 is a graph showing the results of analysis of the effect of the peptide of Example 1 on inhibiting IFN-γ expression and TNF-α expression, and FIG. 4 is a graph showing the results of analysis of the effect of the peptide of Example 1 on inducing TGF-β1 expression. In FIGS. 3 and 4, the x axis represents the control group {(−)}, the negative control group (anti-CD28), and the treatment group of Example 1 (anti-CD28+Example 1), and in FIGS. 3 and 4, the y axis represents the mRNA expression level as the percentage relative to GAPDH {cytokines/GAPDH (%)}.

As shown in FIG. 3, based on the results of evaluation of the expression levels of IFN-γ and TNF-α, known to generate insulitis, each expression level was reduced compared to the negative control group. Therefore, it can be confirmed that the peptide of Example 1 inhibited the expression of IFN-γ and TNF-α, indicating that the development of insulitis was inhibited, thus effectively treating and/or preventing insulitis.

As shown in FIG. 4, based on the results of evaluation of the expression level of TGF-β1 known to affect protection of the pancreas from insulitis, the expression level was increased compared to the negative control group. Therefore, it can be confirmed that the peptide of Example 1 induced the expression of TGF-β1, thereby protecting the pancreas from insulitis, thus effectively treating and/or preventing insulitis.

Accordingly, it can be confirmed that the peptide of Example 1 is effective at the treatment and/or prevention of insulitis by inhibiting IFN-γ expression and TNF-α expression and/or inducing TGF-β1 expression.

In conclusion, the peptide or pharmaceutically acceptable salt thereof according to the present invention is capable of exhibiting a therapeutic and/or prophylactic effect of insulitis by inhibiting IFN-γ expression, inhibiting TNF-α expression, and/or inducing TGF-β1 expression. Ultimately, it can be concluded that the peptide or pharmaceutically acceptable salt thereof according to the present invention is capable of treating and/or preventing type 1 diabetes.

<Comparative Example 1 and Comparative Example 2> Preparation of Peptide

In order to evaluate whether a portion of the peptide of Example 1 exhibits activity, the peptide of Comparative Example 1 and the peptide of Comparative Example 2, comprising the amino acid sequences corresponding to a portion of the amino acid sequence of the peptide of Example 1, were prepared. The peptide of Comparative Example 1 and the peptide of Comparative Example 2 were a peptide (GAGAGY) composed of 6 amino acids sequentially from the C-terminus of the amino acid sequence (YGAGAGAGY) of the peptide of Example 1, and a peptide (YGAGAG) composed of 6 amino acids sequentially from the N-terminus thereof, respectively. The peptide of Comparative Example 1 and the peptide of Comparative Example 2 were manufactured in the same manner as the peptide of Example 1 based on the amino acid sequence shown in Table 3 below.

TABLE 3

| | Amino acid sequence | SEQ ID NO: |
|---|---|---|
| Comparative Example 1 | GAGAGY | 10 |
| Comparative Example 2 | YGAGAG | 11 |

In Table 3, Y represents tyrosine (Tyr), G represents glycine (Gly), and A represents alanine (Ala).

<Comparative Experiment> Evaluation of Peptide Effects of Comparative Example 1 and Comparative Example 2

In order to evaluate whether the peptides of Comparative Examples 1 and 2 are effective at inhibiting IFN-γ expression and TNF-α expression and inducing TGF-β1 expression as in the peptide of Example 1, the following experiment was conducted.

The present experiment was performed in the same manner as in Example 2-3, with the exception that the peptide of Comparative Example 1 or the peptide of Comparative Example 2 was used in lieu of the peptide of Example 1. The results thereof are shown in FIGS. 5 and 6.

FIG. 5 is a graph showing the results of analysis of the effects of the peptides of Comparative Examples 1 and 2 on inhibiting IFN-γ expression and TNF-α expression, and FIG. 6 is a graph showing the results of analysis of the effects of the peptides of Comparative Examples 1 and 2 on inducing TGF-β1 expression. In FIGS. 5 and 6, the x axis represents the control group {(−)}, the negative control group (anti-CD28), the treatment group of Comparative Example 1 (anti-CD28+Comparative Example 1), and the treatment group of Comparative Example 2 (anti-CD28+ Comparative Example 2), and in FIGS. 5 and 6, the y axis represents the mRNA expression level as the percentage {cytokines/GAPDH (%)} relative to GAPDH.

As shown in FIG. 5, based on the results of evaluation of the expression levels of IFN-γ and TNF-α, known to generate insulitis, the expression level thereof in each of the treatment group of Comparative Example 1 and the treatment group of Comparative Example 2 did not greatly change compared to the negative control group, and the treatment group of Comparative Example 2 was instead found to increase the expression level of TNF-α. Moreover, as shown in FIG. 6, based on the results of evaluation of the expression level of TGF-β1 known to affect protection of the pancreas from insulitis, the expression level thereof in each of the treatment group of Comparative Example 1 and the treatment group of Comparative Example 2 did not greatly change compared to the negative control group. From these results, it can be seen that the peptides of Comparative Example 1 and Comparative Example 2 did not exhibit effects of inhibiting IFN-γ expression, inhibiting TNF-α expression, and inducing TGF-β1 expression, unlike the peptide of Example 1.

Based on the above results, it can be concluded that the entirety of the peptide of Example 1, not a portion thereof, is effective at inhibiting IFN-γ expression and TNF-α expression and inducing TGF-β1 expression, and has an effect on insulitis and type 1 diabetes.

<Preparation Example 1> Preparation of Injectable Solution 10 mg of the peptide prepared in the same manner as in Example 1 was dissolved in PBS to make 1 ml of a solution. This solution was charged in an ampoule for injection to afford an injectable solution.

INDUSTRIAL APPLICABILITY

The present invention is effective at treating or preventing insulitis. Moreover, the present invention is effective at treating or preventing type 1 diabetes. Therefore, the present invention is industrially applicable.

The invention claimed is:

1. A method of treating or preventing insulitis, comprising administering an effective amount of a pharmaceutical composition to a subject in need thereof, wherein the pharmaceutical composition comprises a peptide consisting of the amino acid sequence of SEQ ID NO:1 or the pharmaceutically acceptable salt thereof.

2. The method of claim 1, wherein the treating or preventing insulitis is due to at least one selected from the group consisting of inhibition of IFN-γ expression, inhibition of TNF-a expression, induction of TGF-B1 expression, and a combination thereof.

3. A method of treating or preventing type 1 diabetes, comprising administering an effective amount of a pharmaceutical composition to a subject in need thereof, wherein the pharmaceutical composition comprises a peptide consisting of the amino acid sequence of SEQ ID NO: 1 or the pharmaceutically acceptable salt thereof.

4. The method of claim 3, wherein the type 1 diabetes is caused by insulitis.

5. The method of claim 3, wherein the treating or preventing type 1 diabetes is due to at least one selected from the group consisting of inhibition of development of insulitis, reduction of development of insulitis, and a combination thereof.

* * * * *